United States Patent
Doyle et al.

[19]

[11] Patent Number: 5,879,158
[45] Date of Patent: Mar. 9, 1999

[54] ORTHODONTIC BRACKETING SYSTEM AND METHOD THEREFOR

[76] Inventors: Walter A. Doyle, 924 Witthuhn Way, Lexington, Ky. 40503; Steven Franseen, 10196 West Keene Ave., Denver, Colo. 80235

[21] Appl. No.: 858,980

[22] Filed: May 20, 1997

[51] Int. Cl.$^6$ .................................................. A61C 3/00
[52] U.S. Cl. ............................................................. 433/24
[58] Field of Search .................................. 433/24, 8, 229

[56] References Cited

U.S. PATENT DOCUMENTS

| | | | |
|---|---|---|---|
| 5,139,419 | 8/1992 | Andreiko et al. | 433/24 |
| 5,368,478 | 11/1994 | Andreiko et al. | 433/24 |
| 5,518,397 | 5/1996 | Andreiko et al. | 433/24 |
| 5,533,895 | 7/1996 | Andreiko et al. | 433/24 |

*Primary Examiner*—Ralph A. Lewis
*Attorney, Agent, or Firm*—Emrich & Dithmar

[57] ABSTRACT

From a negative impression of a patient's teeth, a positive hard duplicate pattern such as a stone model of the teeth is made. A digitized three dimensional coded image of the teeth is then generated by means of a coordinate measuring machine or by laser scanning. The central axis of each tooth is then displayed in an exploded image of the set of teeth and each tooth is moved in virtual space to a desired position and orientation using torque, tip and angulation values as well as in/out position information provided by the selected orthodontic bracket system. The optimum position of each tooth-mounted orthodontic appliance bracket and its attachment point to its associated tooth for moving the tooth to a desired orientation and position is then determined using the digitized coded images of each tooth including its central axis in its initial and final desired position and orientation. Using this bracket attachment information for each tooth, the shape and contour of a bracket attachment jig is determined for each tooth and this information in digital form is used to fabricate a plurality of such jigs under computer control such as by using a computer numeric control (CNC) milling machine for attaching an off-the-shelf, conventional orthodontic bracket to each tooth. Conventional archwires attached to the upper and lower optimally positioned brackets urge each tooth to its respective desired position and orientation with minimal subsequent manipulation and adjustment of the archwires by the orthodontist.

5 Claims, 10 Drawing Sheets

FROM FIG. 3a

30 UNBLANK SCREEN TO DISPLAY UPPER AND LOWER TEETH, WITH EACH TOOTH DISPLAYED WITH A LONGITUDINAL AXIS THROUGH ITS CENTER

31 MOVE EACH BRACKET ALONG ITS RESPECTIVE ARCHWIRE TO A POSITION ADJACENT ITS ASSOCIATED TOOTH ON DISPLAY

32 DISTRIBUTE TEETH EVENLY AND SYMMETRICALLY ALONG ARCH WIRE

34 GENERATE AND DISPLAY AXIAL LINE RUNNING FROM TIP TO TIP FOR EACH TOOTH

36 COMPARE AXIAL LINE OF TOOTH WITH CODED TORQUE INFORMATION FOR BRACKET

38 IS THERE A DIFFERENCE BETWEEN AXIAL LINE AND CODED IMAGE OF TOOTH?

40 NEXT TOOTH

42 TIP TOOTH TO ITS CORRECT TORQUE VALUE

44 COMPARE AXIAL LINE OF TOOTH WITH CODED ANGULATION INFORMATION FOR BRACKET

46 IS THERE A DIFFERENCE BETWEEN AXIAL LINE OF TOOTH AND CODED ANGULATION INFORMATION FOR BRACKET

48 NEXT TOOTH

ORTHODONTIC BRACKETING SYSTEM AND METHOD THEREFOR

FIELD OF THE INVENTION

This invention relates generally to the use of orthodontic appliances for moving teeth into a desired configuration and alignment and is particularly directed to the use of custom designed jigs for precisely attaching an orthodontic bracket to each tooth in a desired position for optimum positioning of each tooth by an archwire attached to each bracket with minimal subsequent adjustment and manipulation of the archwire and bracket combination.

BACKGROUND OF THE INVENTION

Orthodontic braces comprised of a plurality of brackets and an archwire for applying the appropriate force to a patient's teeth are commonly used to move the teeth into a desired configuration or alignment. Each bracket is firmly attached to a respective tooth and serves as a handle on the tooth for the force-producing archwire. The forces applied by the archwires through the brackets are gradually adjusted by the dentist to move and/or re-orient each tooth in a desired manner. These forces applied to the teeth move the teeth gradually toward the positions and/or orientations desired by the orthodontist. Different bracket arrangements are available to the dentist, with the dentist generally selecting a particular bracket system based upon the patient's specific pre-treatment malocclusion (condition requiring treatment), dental surface morphology, and facial type. However, the various bracket systems are not custom designed for each tooth, nor are they configured for the individual patient's jaw bone relationships or functional movement patterns. Rather, bracket and archwire configurations are of a generally generic design with the teeth in a static position. For example, the slots which hold the wire in the different brackets are substantially uniform. Because of this, the forces of the archwire on the teeth must be adjusted by bending or otherwise distorting the archwires.

The inability to adapt to the individual patient's condition has rendered prior approaches generally time consuming, expensive and of limited precision. For example, it is frequently necessary to replace the brackets attached to the patient's teeth as treatment progresses. In addition, prior approaches have required a considerable amount of work by the orthodontist over an extended period of time to progressively adjust the forces applied against the teeth. Moreover, the bending and distortion of the archwire to adjust the forces on the patient's teeth is largely accomplished on an empirical basis based in substantial part upon the experience of the orthodontist. Even the experienced orthodontist has difficulty in bending and twisting the archwire precisely so that the proper force is applied to the brackets attached to each of the patient's teeth. Moreover, unless the bracket is attached at the proper location on the tooth, precise positioning and alignment of the set of teeth is virtually impossible. Current approaches require the orthodontist to visually select the optimum bracket location and then attempt to locate the bracket accordingly on the tooth. This imprecise "eyeballing" approach limits the degree of alignment of the repositioned teeth and generally ignores functional movement of the mandible (lower jaw).

In an ideally functioning occlusion, certain anatomic structures maintain interactive relationships to each other. For example, as the occlusal plane steepens (gets higher posteriorly), the angulation of the upper incisors becomes more vertical. Other related structures are the cusp angulations of the posterior teeth and the steepness of the articular eminence of the mandibular fossa. All of these relationships can be measured and expressed numerically.

In addition, all of these functional relationships undergo adaptation when the relationships of the upper and lower jaw bones are varied in the anterior-posterior plane. For example, if the lower jaw is too far forward in relation to the upper (Class III), the occlusal plane is lower posteriorly and all the other relationships must change proportionately in order to maintain a smoothly functioning occlusion without traumatic interference. FIGS. 1 and 2 illustrate these relationships. These relationships have been published and are generally accepted knowledge. However, the great variation of individual tooth anatomy and the number of existing variables have precluded such idealization of orthodontic treatment goals.

The present invention addresses the aforementioned limitations of the prior art by allowing the orthodontist not only to allow inclusion of variable tooth anatomy into idealized bracket placement, but also to include for the first time other factors which determine a non-traumatic, properly functioning occlusion for a specific individual. The present invention contemplates an orthodontic bracketing system and method therefor which employs a digital computer as well as a video display for custom designing a set of orthodontic jigs, or positioning fixtures, for engaging each bracket and tooth combination for optimum positioning of the bracket on the tooth for subsequent repositioning and/or reorientation of the tooth by means of an archwire. Digital data of the size, shape and contour of each tooth is measured, recorded and displayed to permit the central axis of each tooth to be viewed by the orthodontist and to be moved in virtual space using torque, tip and angulation values as well as in/out position information to relocate and/or reorient the tooth, as desired. Using the measured and stored digital data representing the size, shape and contour of each tooth, the relationship of the jaw bone and the movement path of the lower jaw, a computer controlled milling machine forms each positioning jig to match its associated tooth to ensure optimum positioning of the orthodontic bracket on the tooth.

OBJECTS AND SUMMARY OF THE INVENTION

Accordingly, it is an object of the present invention to provide an improved orthodontic system and method for repositioning and/or reorienting a patient's teeth as desired.

It is another object of the present invention to provide for the precise alignment of a patient's teeth using a conventional orthodontic bracket system in combination with computer graphics and a computer numeric control milling machine.

Yet another object of the present invention is to provide apparatus and a method for attaching an orthodontic bracket to a tooth at the location on the tooth which provides the desired repositioning of the tooth by an archwire attached to the bracket with minimal subsequent manipulation and reconfiguring of the archwire.

A further object of the present invention is to provide a set of custom formed positioning jigs for attaching each of a plurality of orthodontic brackets to a location on a respective tooth for repositioning and/or re-orienting each tooth as desired by means of an archwire attached to the set of brackets.

A still further object of the present invention is to allow the functional surfaces of the teeth to be positioned in harmony with the anatomy and movement patterns of the jaws to each other.

This invention contemplates a method for installing conventional orthodontic brackets and an archwire on a set of teeth, the method comprising the steps of forming a positive hard duplicate pattern of a patient's set of teeth; scanning the positive hard duplicate pattern for providing a digitized three dimensional coded video image of the set of teeth and storing the digitized coded video image in a memory; displaying a center axis of each tooth in the set of teeth, wherein the center axis extends between a root portion and a crown portion of the tooth; determining differences between the position and orientation of the center axis of each tooth and torque, tip and angulation values for each tooth representing a desired position and orientation of the tooth for a selected set of orthodontic brackets; determining differences between the digitized three dimensional video image and a statistically average tooth for each tooth; determining an optimum position of each bracket on an associated tooth for moving the tooth to the desired position and orientation; determining a size and shape of a positioning jig for each bracket and tooth combination for optimum positioning of each bracket on a respective tooth for moving the tooth to the desired position and orientation; attaching each jig to an associated bracket and installing each jig and bracket combination on a respective tooth in said optimum position; removing each jig from its associated bracket; and attaching an archwire to the brackets.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIGS. 3a–3e are a series of flow charts illustrating the sequence of steps in carrying out the method of installing orthodontic brackets of the present invention;

DETAILED DESCRIPTION OF THE PREFERRED EMBODIMENT

Referring to FIGS. 3a–3e, there is shown a series of flow charts illustrating the sequence of steps involved in carrying out the inventive orthodontic bracket measuring, fabrication and installation method of the present invention. Some of the steps, or operations, indicated in the flow charts are carried out under the control of a microcomputer using instructions stored in the microcomputer as described below, while other operations are carried out by a person practicing the invention. In FIGS. 3a–3e, a diamond symbol indicates a decision point based upon the comparison of binary input signals and a rectangle indicates an instruction or set of instructions to the microcomputer or an operation carried out by a person practicing the invention. A detailed description of the method set forth in FIGS. 3a–3e follows, with additional description directed to apparatus used in carrying out the inventive method provided.

Figure 1:
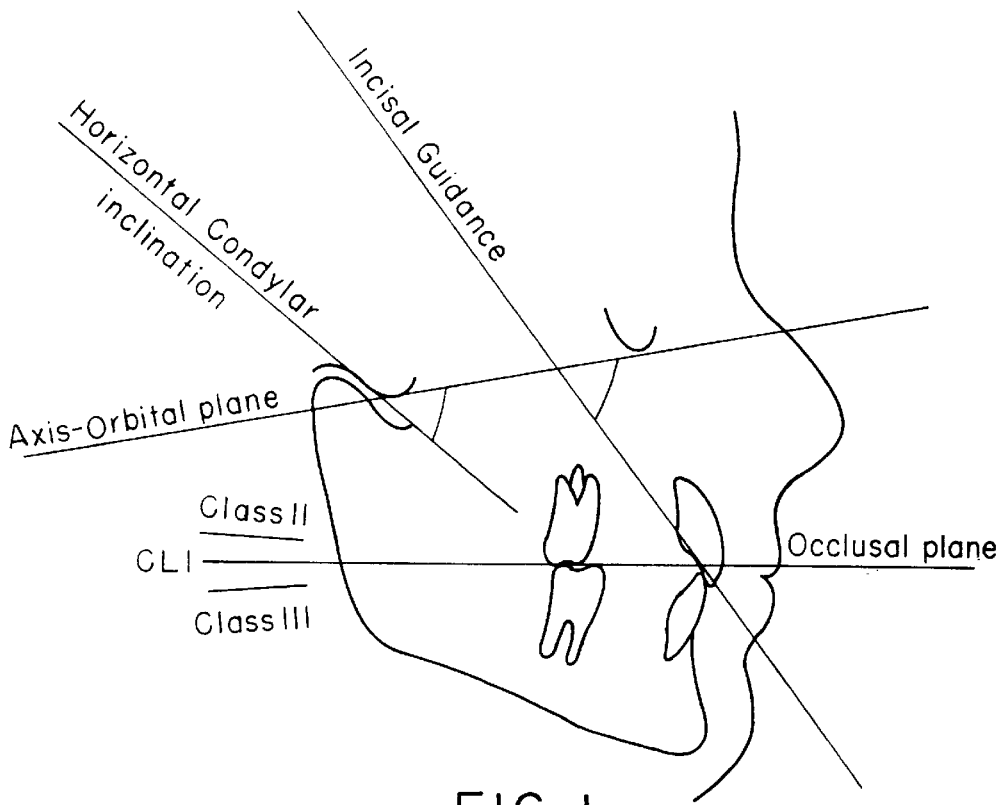
FIGS. 1 and 2 illustrate the relationship between the upper and lower jaws and the occlusion between adjacent teeth.
Figure 2:
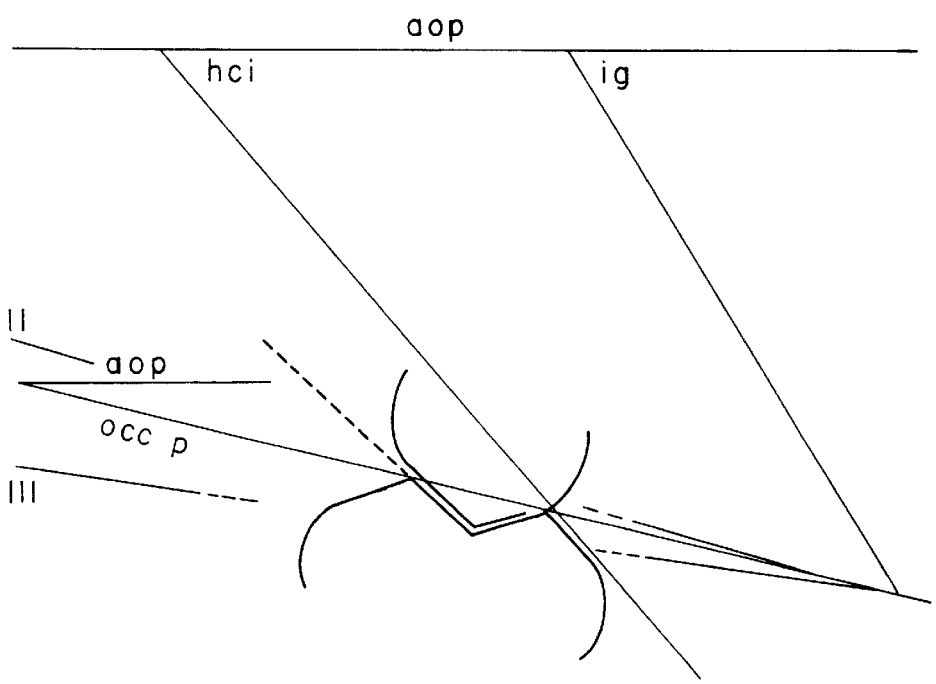
Figure 3A:
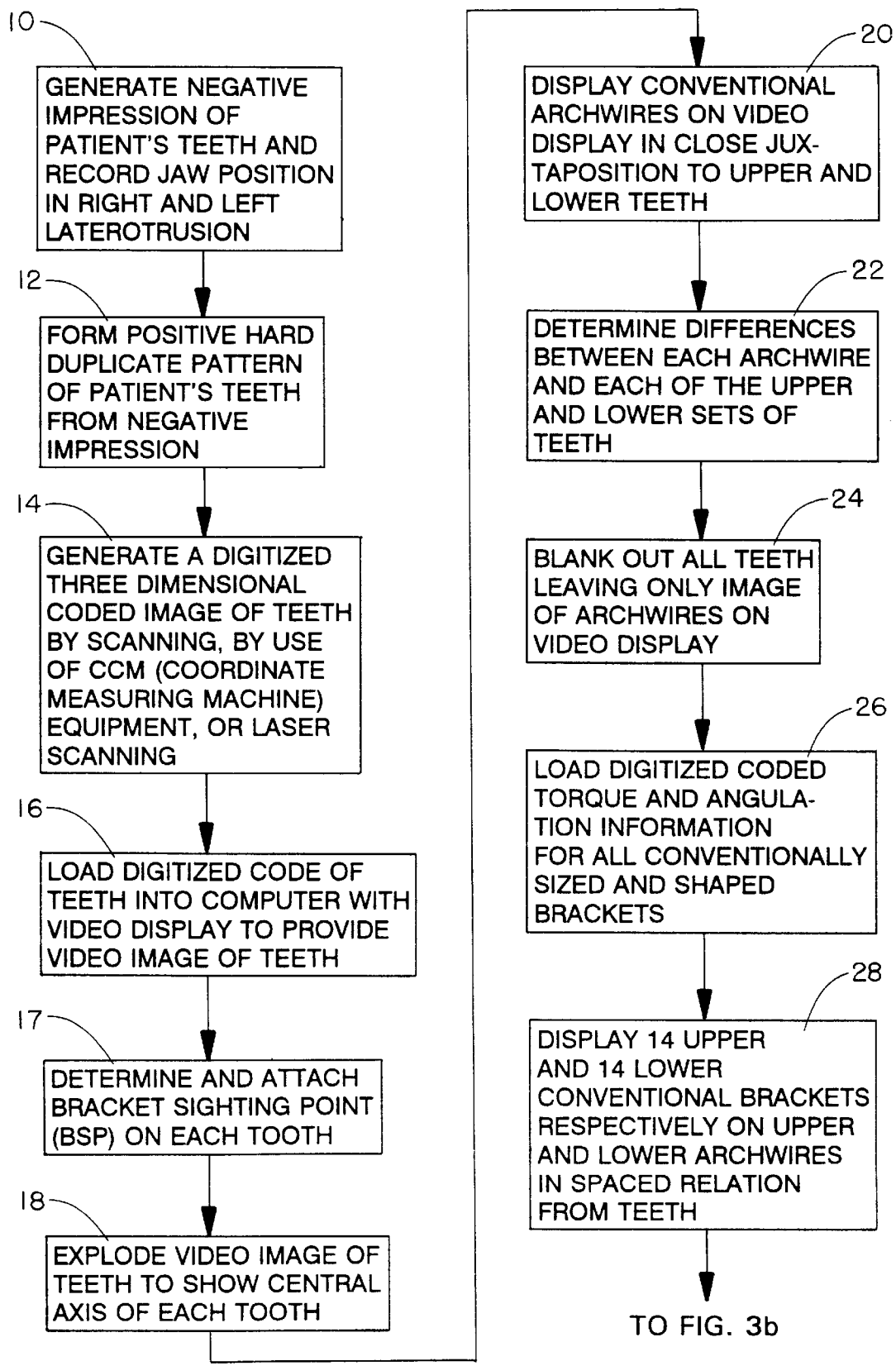
Figure 3C:
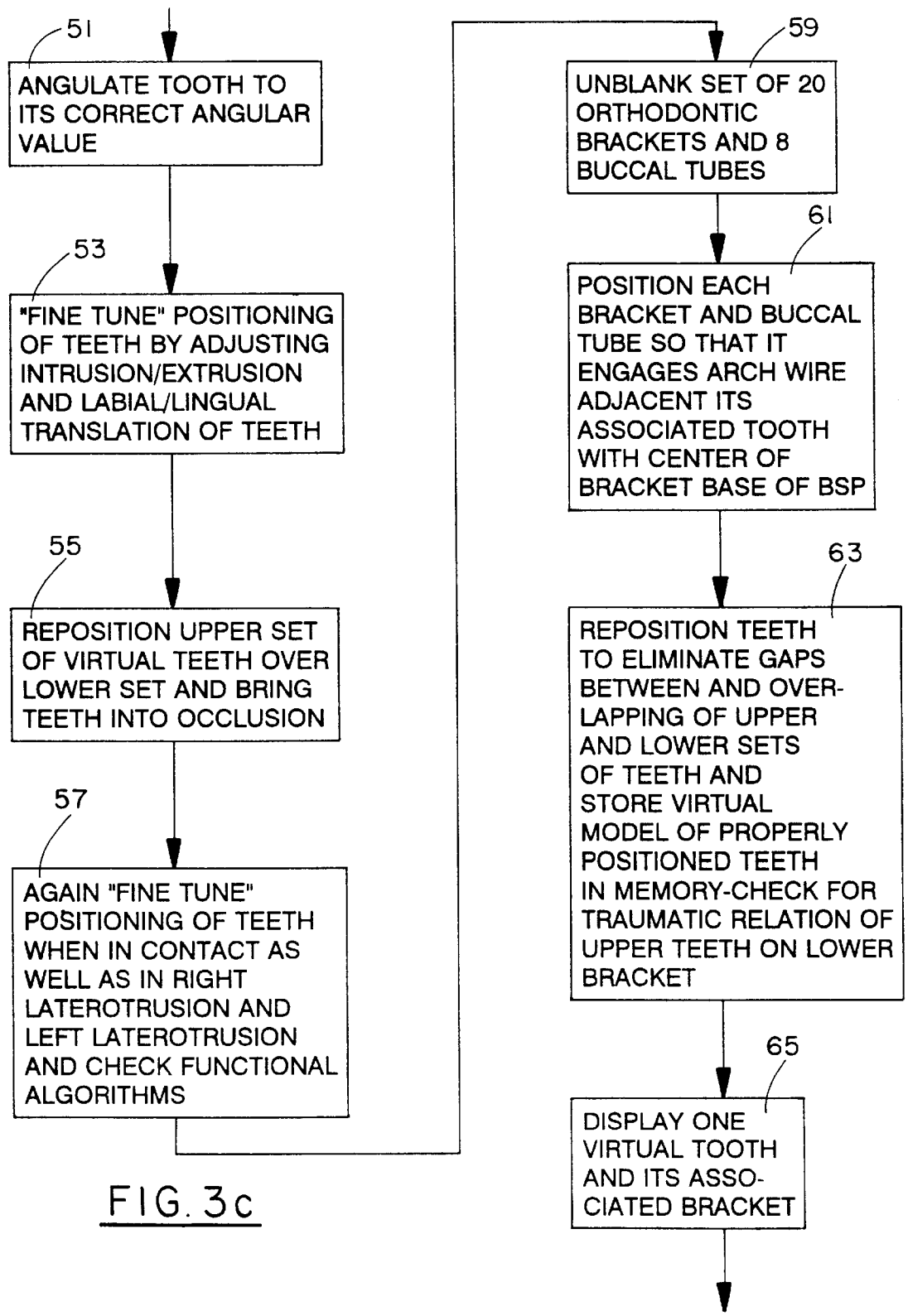
Figures 3D, 3E:
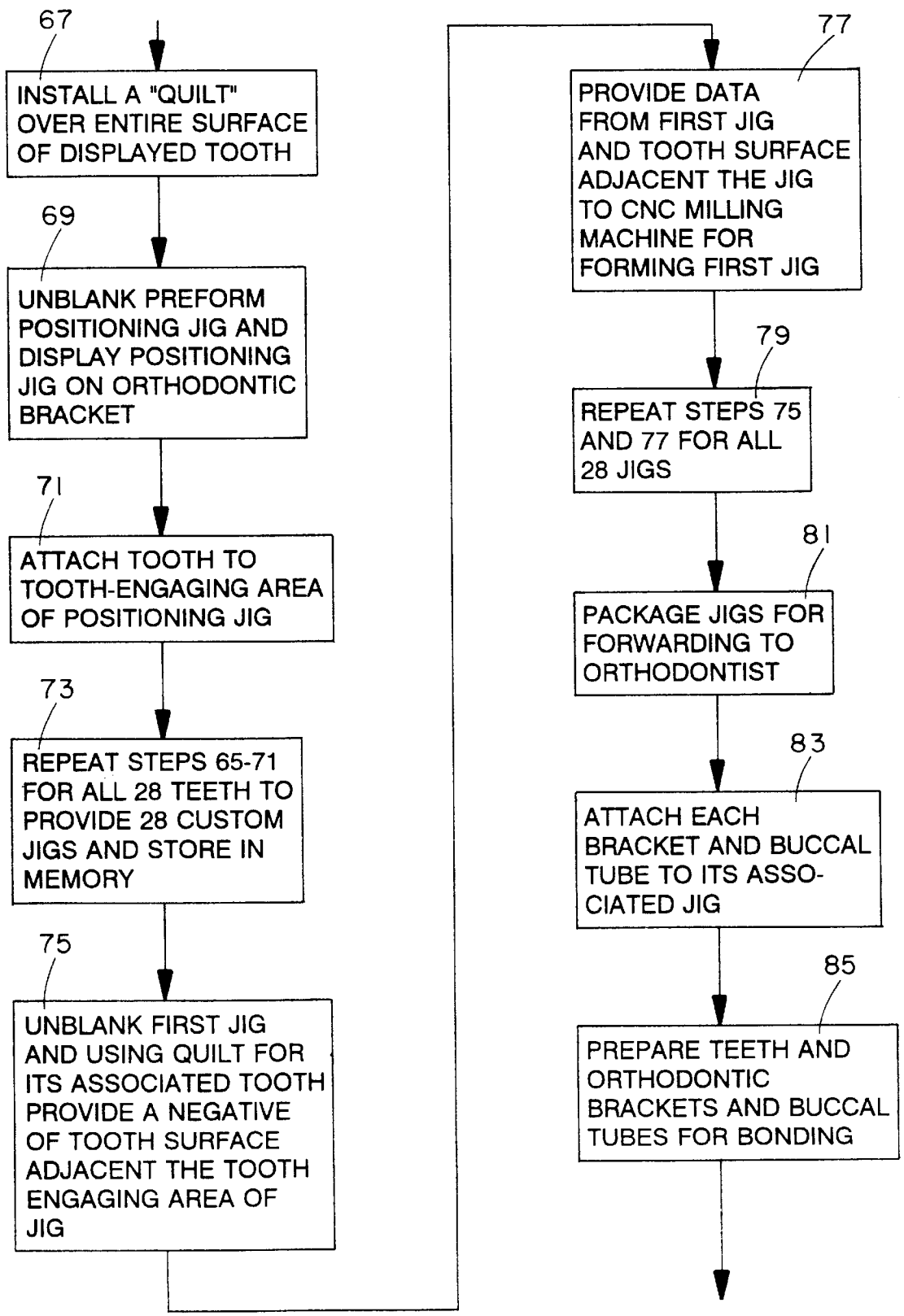
Figure 3E:
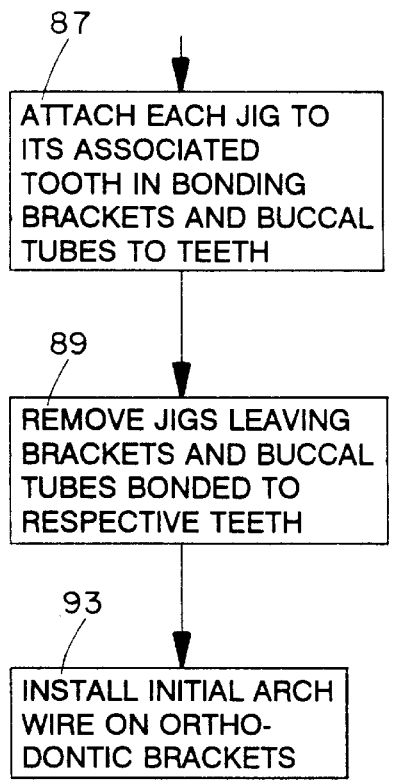
Figure 4:
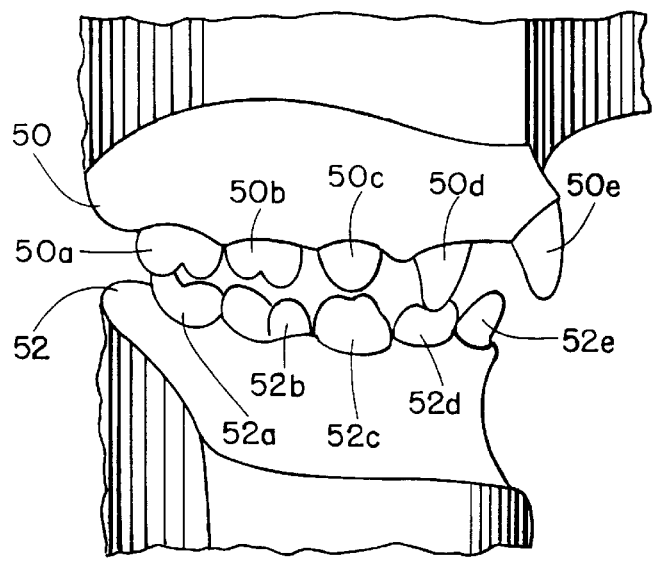
FIG. 4 is a side elevation view of a positive mold of an upper and a lower set of teeth for use in the orthodontic bracketing system and method therefor of the present invention.

As shown in FIG. 3a, the first step 10 in carrying out the inventive orthodontic bracket measuring, fabrication and installation method involves the generation of a negative impression of the patient's upper and lower teeth. An alginate impression is preferably made of both arches of the patient to determine how the upper and lower teeth relate to each other and bite registrations are taken to show how they move when functioning in right and left laterotrusion. Next, at step 12 a positive hard duplicate pattern, or positive mold, of the patient's teeth is made from the negative impression. FIG. 4 is a side elevation view of a typical upper positive hard duplicate pattern 50 and a lower positive hard duplicate pattern 52 of a patient's teeth, where the upper teeth are shown as elements 50a–50e and the lower teeth are shown as elements 52a–52e. The upper and lower positive hard duplicate patterns 50, 52 of the patient's upper and lower teeth are typically comprised of a hard dense material and are sometimes referred to as a "stone model." The positive mold may be formed by pouring a fluid, curable material into a form comprised of negative impressions of the patient's upper and lower teeth. The upper and lower positive hard duplicate patterns 50,52 are mounted on an articulator which maintains the two duplicate patterns in anatomic relation to each other. The laterotrusion bite registrations allow adjustment of the articulator to mimic the jaw movement of the patient's lower jaw in relation to the upper jaw. This also allows calculations to be made for the horizontal condyle inclinations, the steepness of the occlusal plane and the ideal function relations of the lingual surface of the anterior teeth.

Figure 5A:
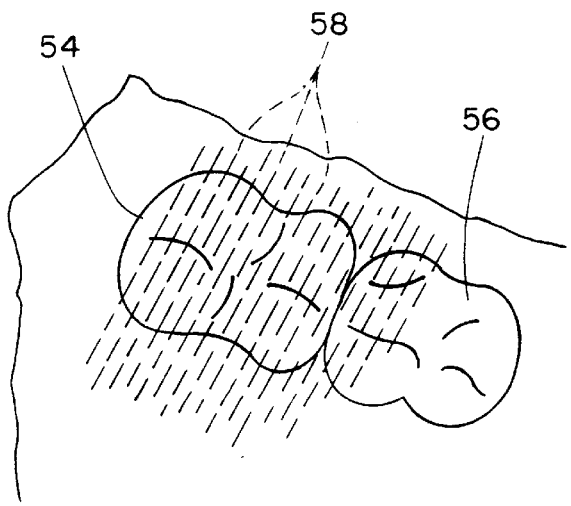
FIGS. 5a and 5b are respectively top plan and side elevation views of a partial set of teeth showing the manner in which the teeth are scanned by a laser beam for generating a digitized three dimensional coded image of the teeth for use in the present invention.
Figure 5B:
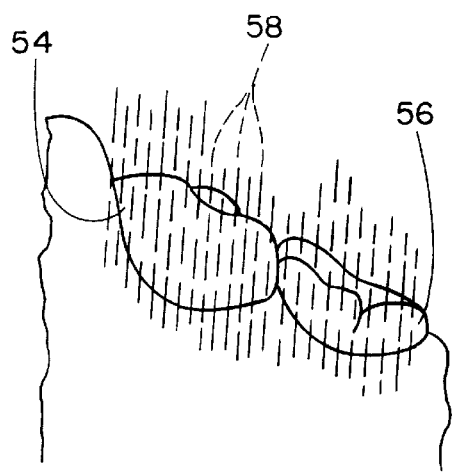

The next step 14 in the inventive process involves generating a digitized three dimensional coded virtual image of the patient's upper and lower teeth and gums by scanning the positive hard duplicate pattern of the teeth by conventional means such as a coordinate measuring machine (CCM) or by laser scanning. The latter approach of converting the stone model of the patient's teeth to a digitized three dimensional coded image is shown in simplified schematic diagram form in FIGS. 5a and 5b. In these figures, a laser beam 58 is shown in the form of a series of parallel dotted lines scanning first and second teeth 54 and 56. In FIG. 5a, the laser beam 58 is aligned generally horizontally and scans over the teeth 54 and 56 in moving horizontally either forward to aft through a series of vertically spaced planes. FIG. 5b shows a laser beam 58 aligned generally vertically also being displaced either rearwardly or forwardly relative to the first and second teeth 54 and 56 as a series of horizontally spaced dotted lines. A pair of laser scanning arrays as shown in FIGS. 5a and 5b provides a digitized three dimensional coded image of the set of teeth.

Figure 6:
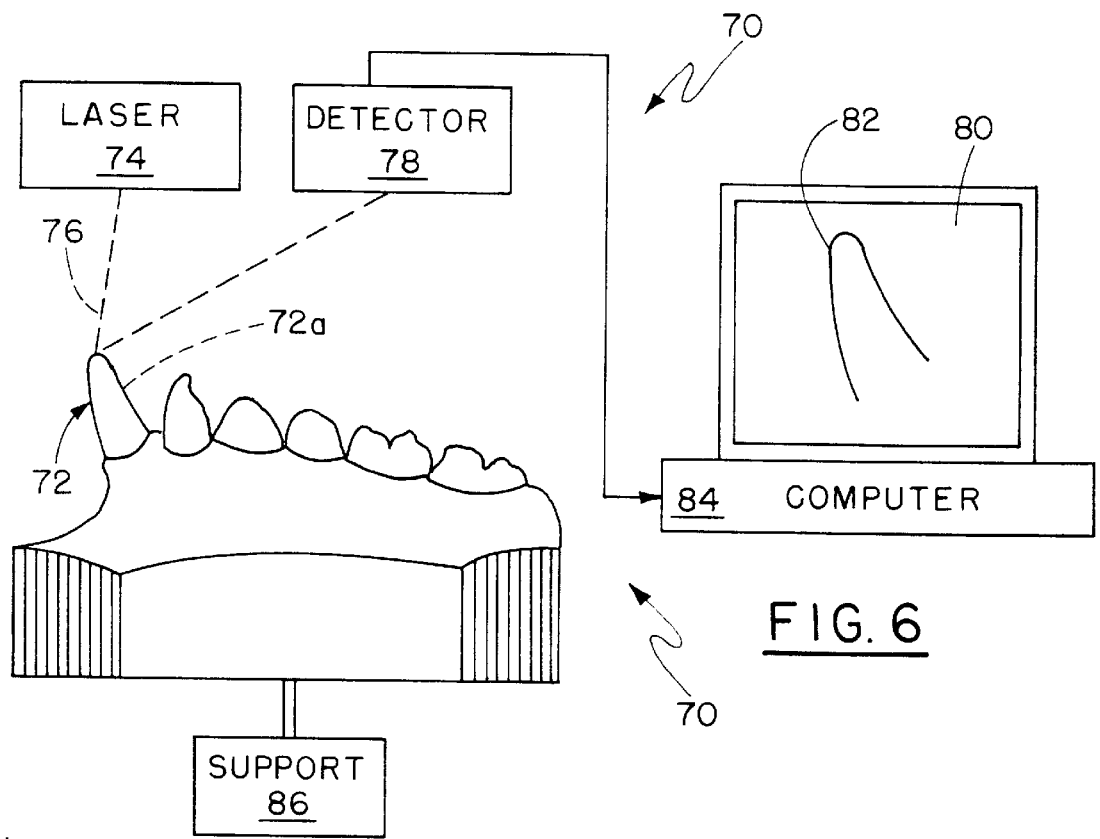
FIG. 6 is a simplified schematic diagram of an arrangement for laser scanning of a set of teeth in generating a digitized three dimensional coded image of the teeth for use in the present invention.

Referring to FIG. 6, there is shown a simplified schematic diagram of a laser scanning and display system 70 for providing a digitized three dimensional coded image of a positive hard duplicate pattern of a set of teeth 72. In the figure, a first tooth 72a is shown being scanned by a laser beam 76 (shown in dotted line form) from a laser 74. Laser 74 is attached to and supported by a displacement mechanism, which is not shown in the figure for simplicity, for orienting the laser beam 76 either vertically or horizontally and displacing the laser for scanning the positive hard duplicate pattern 72 of the set of teeth. The positive hard duplicate pattern 72 of the set of teeth is attached to a support mechanism 86 which is adapted to linearly displace and/or rotate the set of teeth, as desired. The laser scanning and display system 70 further includes a detector 78 for detecting the laser beam 76 as it is reflected from the various teeth in the positive hard duplicate pattern 72 of teeth for measuring the size, position and shape, or contour, of each tooth. The laser beam detector 78 provides an input signal representing the size, shape and surface contour of each tooth in the set of teeth to a computer 84 which, in turn, provides appropriate digital video signals to a video display 80 for presenting a video image 82 of tooth 72a being scanned by the laser beam 76 on the display. In this approach, as well as in the approach described in the following paragraph and shown in FIG. 7, a conventional triangulation method may be used to convert a change in position of the detector 78 to a change in distance between the scanning and display system 70 and the set of teeth 72. The data provided by detector 78 to computer 84 represents a full detailed three dimensional image of the patient's upper and lower jaws with the teeth in their original, uncorrected positions.

Figure 7:
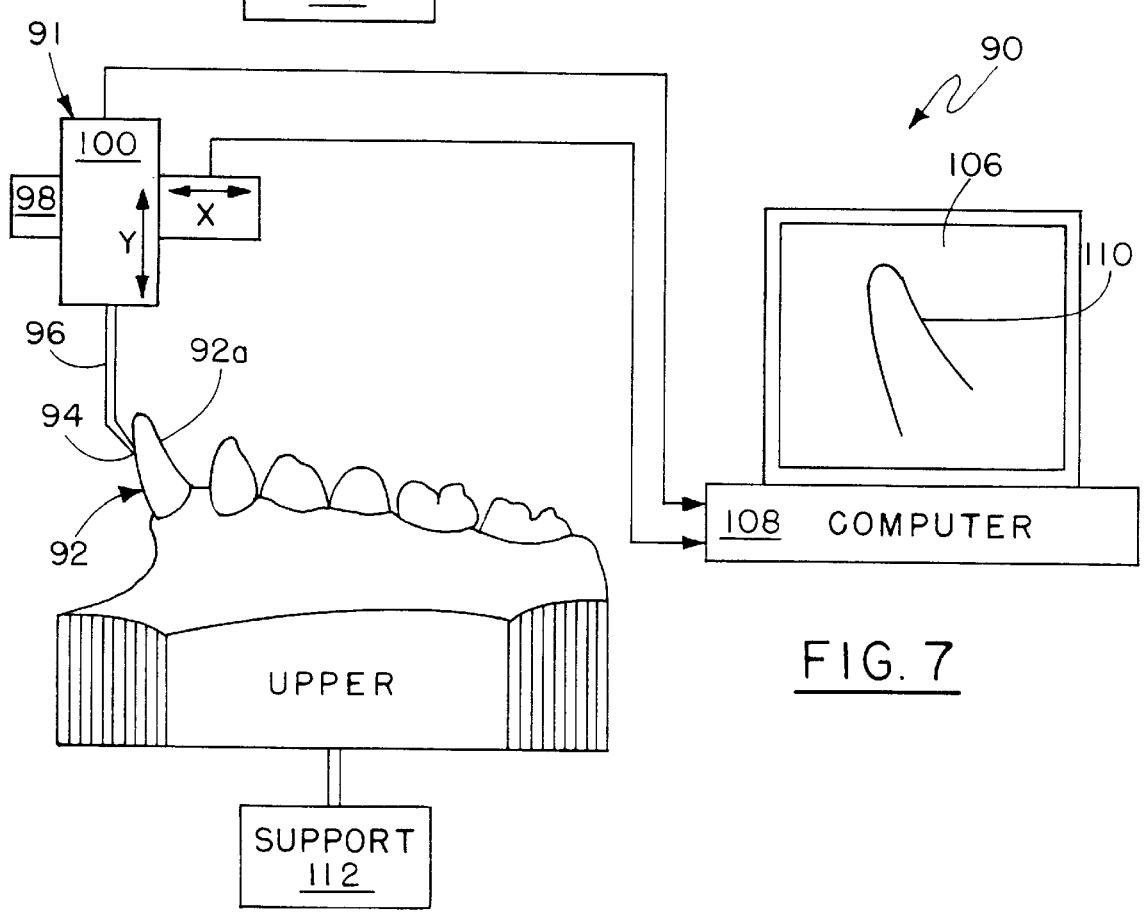
FIG. 7 is a simplified schematic diagram of a coordinate measuring machine for use in measuring and generating a digitized three dimensional coded image of the teeth for use in the present invention.

Referring to FIG. 7, there is shown in simplified block and schematic diagram form another arrangement for providing a digitized three dimensional coded image of each of the teeth in a positive hard duplicate pattern 92 of a set of teeth. In the arrangement of FIG. 7, a coordinate measuring and display system 90 includes a coordinate measuring machine (CCM) 91. The coordinate measuring machine 91 includes a measurement probe 96 having a probe tip 94 on the distal end thereof. Measurement probe 96 is coupled to and displaced by an X-axis position transducer 98 and a Y-axis position transducer 100. Measurement probe 96 is further coupled and displaced by a Z-axis position transducer which is not shown in the figure for simplicity. The three axis position transducers measure and record the size, shape and contour of each of the teeth as the measurement probe tip 94 traces over the surfaces of the teeth. This information is provided to a computer 108 which provides appropriate digital signals to a video display 106 for displaying the video image 110 of a tooth 92a in the positive hard duplicate pattern 92 of the set of teeth. The positive hard duplicate pattern 92 is mounted to and, if desired, may be displaced by a support mechanism 112. By scanning the surfaces of the various teeth of the positive hard duplicate pattern 92 by means of the coordinate measure machine's probe tip 94, digital information representing the size, shape and contour of each of the teeth may be presented on the video display 106 as well as stored in a digital memory (not shown for simplicity) in computer 108 for subsequent display or further processing. In operation, probe 96 is manually moved or may be automatically displaced so that its tip 94 contacts the surface of the teeth to provide a tooth profile as shown in the profile image 110 of tooth 92a.

After generating a digitized three dimensional coded image of the teeth by laser or mechanical probe scanning, a digitized code of the teeth is loaded into the computer at step 16. With the upper and lower virtual models positioned with occlusal edges of the teeth oriented "up," a bracket sighting point (BSP) is determined by the technician for all 28 teeth at step 17. The BSP is a point on the facial surface of the clinical crown over which the center of the base of a standard orthodontic bracket is to be precisely positioned. The BSP is determined by establishing the vertical axis of the clinical crown. For partially erupted or super erupted teeth, the technician may refer to X-rays of the patient's teeth which will reveal the extent of the clinical crown (or anatomical crown typically minus 1.8 mm). For molars, the BSP is positioned on the mesial buccal cusp. The technician then establishes the mid-transverse plane of each tooth, which is the plane that separates the occlusal half of the clinical crown from the gingival half. The technician then determines the intersection point of the vertical axis and the mid-transverse plane on the labial surface of the crown for each tooth. A BSP is then installed on each tooth so that it becomes integral to that tooth. The BSP then moves with the tooth during subsequent translations and manipulations of the tooth.

Figure 8:
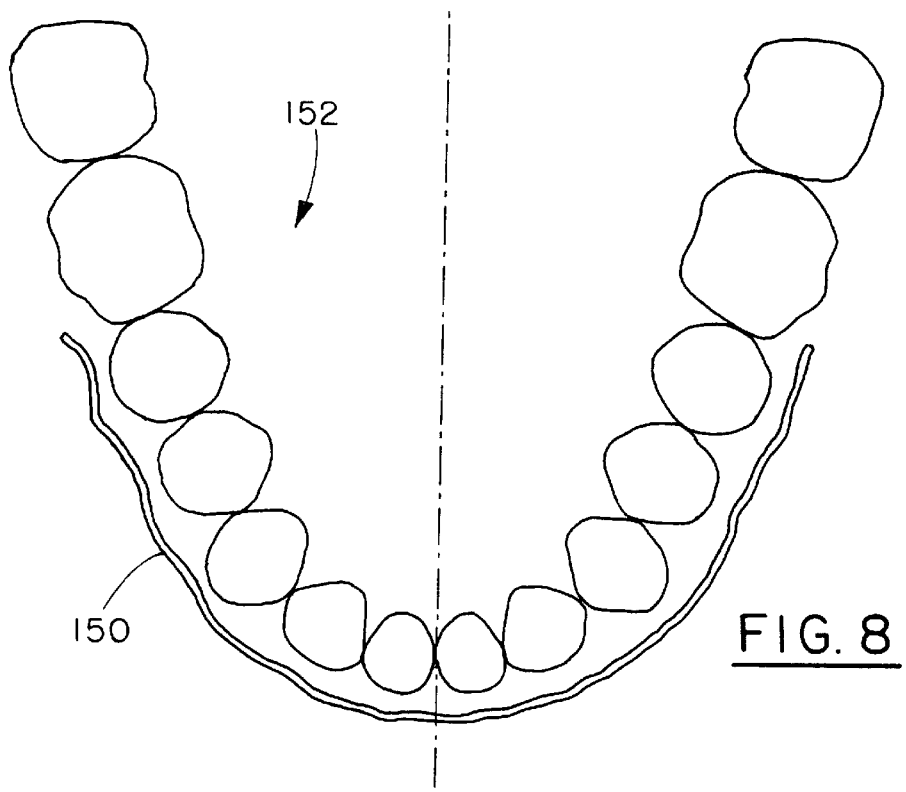
FIGS. 8 and 9 are plan views of a set of teeth respectively illustrating an archwire positioned in closely spaced relation to the teeth and the combination of an archwire and an attached set of orthodontic brackets positioned in closely spaced relation to the teeth.

Next, at step 18 this topographic data in the form of an exploded video image of the teeth is presented on the video display including the central longitudinal axis of each tooth. Storing this data in the computer allows the 3-dimensional rendering of the patient's teeth and gums to be positioned in infinite orientations on the computer monitor as described below. Generating and storing this data also permits each tooth to be independently manipulated relative to the gum and other teeth. At step 20, a conventional archwire 150 is presented on the video display as shown in FIG. 8 in close juxtaposition to the set of teeth 152 scanned, measured and displayed on the video display. The archwires are disposed in a plane described in the following paragraphs. At step 22, differences in the spacing between each archwire and each tooth in its associated set of teeth is determined. This step involves leveling the BSP for each tooth so that each of the 14 BSP's in a set of upper or lower teeth are common to a plane. The overall elevation of this plane relative to the gums is determined by X-ray evaluation of the patient's supporting bone/root structure, and/or is keyed to the existing positions of untreated teeth that describe a desirable pre-treatment positioning of the root in the supporting bone.

The plane may also be "warped" in the region of the posterior teeth to describe a naturally occurring curve known as the "curve of Spee" or warped sagittally to describe a naturally occurring curve known as the "curve of Wilson."

Figure 9:
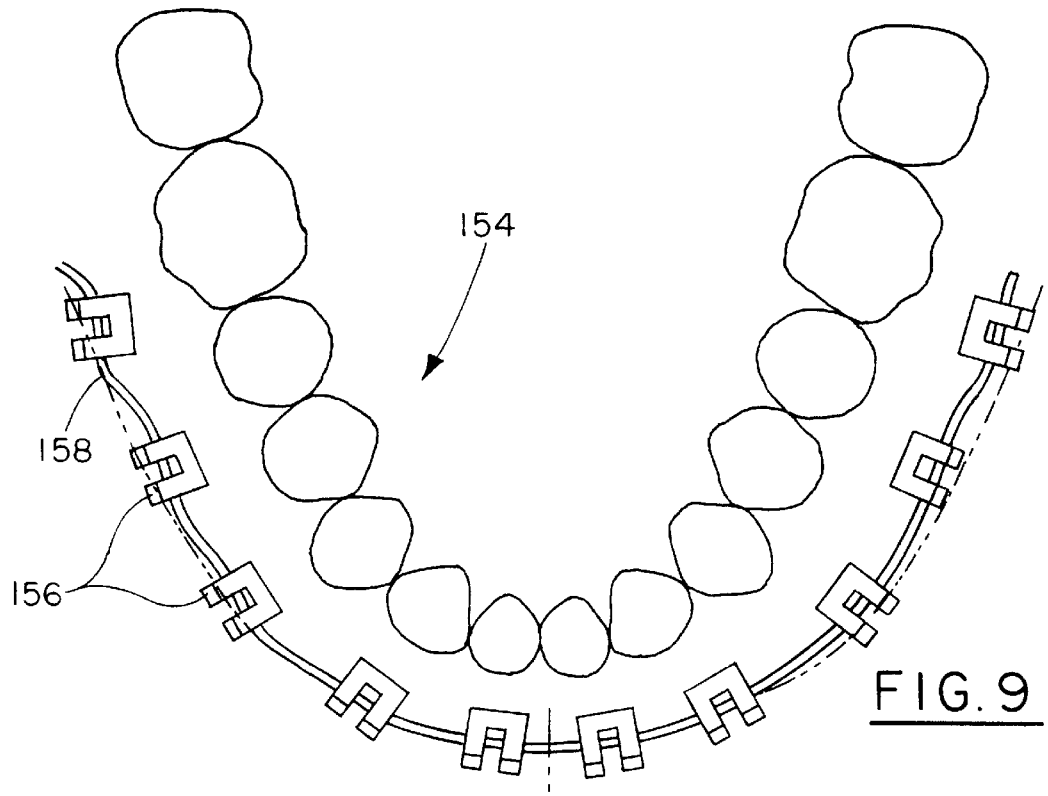

Even though "warped," and technically a "surface," the following discussion will nonetheless refer to this region as a plane. Algorithms can be calculated from the previously stored anatomic and functional movement patterns to properly relate the functional surfaces of the teeth in movement. This allows for more precise positioning of the functional surfaces of the teeth in relation to their movement against each other when eating. All of the teeth are then blanked from the video display at step 24 leaving only an image of the archwire on the video display. This brings the archwires into the 3-D virtual CAD/CAM space. The selection of the specific archwire shape to be used for an individual's treatment is based on the patient's facial type and other orthopedic considerations. Digitized coded torque and angulation information for conventionally sized and shaped orthodontic brackets from the set of orthodontic brackets which has been selected for use is then loaded into the computer at step 26. At step 28, 14 upper and 14 lower conventional orthodontic brackets respectively attached to upper and lower archwires are displayed in spaced relation from an ideally positioned set of teeth 154 as shown in FIG. 9. The video display is then unblanked at step 30 to display the upper and lower sets of teeth, with each tooth displayed in its desired location and orientation and having a longitudinal axis through its center.

Figure 10:
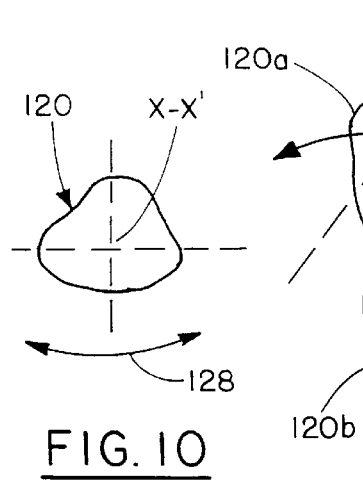
FIGS. 10, 11 and 12 are respectively plan, side elevation and perspective views of a tooth showing the manner in which the tip, angulation and torque of the tooth is corrected using the longitudinal central axis of the tooth as a reference in accordance with one aspect of the present invention.
Figure 11:
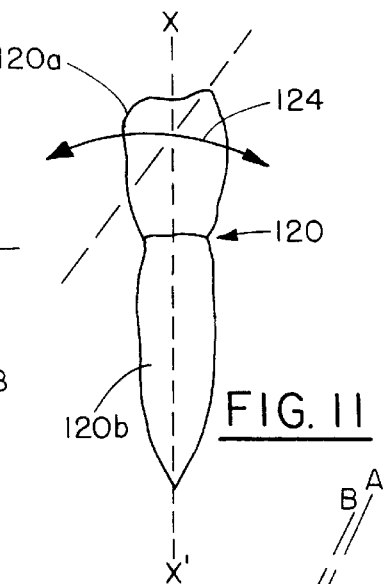
Figure 12:
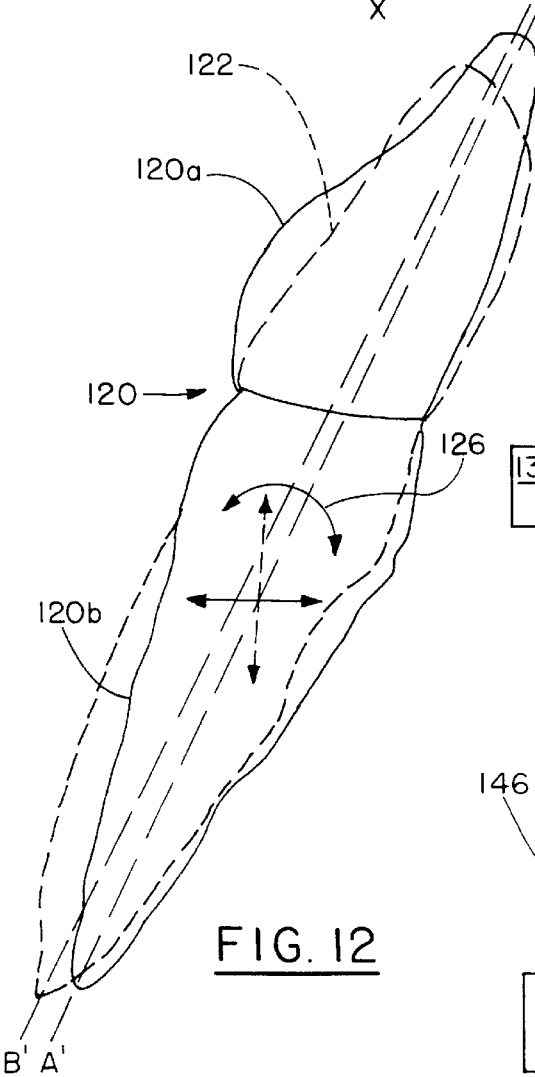

Referring to FIGS. 10, 11 and 12, there are respectively shown top plan, side elevation and perspective views of a tooth illustrating its central longitudinal axis. Tooth 120 shown in FIGS. 10, 11 and 12 includes an upper crown portion 120a and a lower root portion 120b. As shown in FIGS. 10 and 11, the tooth includes a longitudinal central axis X–X' extending the length of the tooth through its center. The tooth 120 may be moved on the video display in opposed directions shown by arrow 128 in FIG. 10 to change the rotation of the tooth. Similarly, the tooth 120 may be displaced in one of two opposed directions shown by arrow 124 in FIG. 11 to change the angulation of the tooth on the video display. Finally, in the perspective view of tooth 120 of FIG. 12, the tooth may be rotated in one of two opposed directions shown by arrow 126 to change the torque of the tooth. In FIG. 12, the center longitudinal axis of the tooth 120 is shown as dotted line A–A'. FIG. 12 presents a comparison of the size, shape and contour of tooth 120 with another tooth 122 (shown in dotted line form) such as a statistically average tooth having a different size, shape and contour. Tooth 122 has a center longitudinal axis represented by dotted line B–B'. Each tooth has an imaginary line extending through its center and between its two opposed tips. Each tooth is shown at step 30 together with its center longitudinal axis as shown in FIGS. 10, 11 and 12.

The next step in the inventive process involves moving each orthodontic bracket along its respective archwire to a position adjacent to its associated tooth, or the tooth to which it is to be bonded, on the video display at step 31. Next, the teeth are distributed on the video display evenly and symmetrically along their respective arch wires at step 32. An axial line running from tip to tip, or from the tip of the tooth's crown to the tip of its root, for each tooth is then displayed on the video display at step 34. The center axial line of each tooth is then compared with coded torque information for the particular orthodontic bracket selected at step 36. The next step at step 38 is to determine if there is a difference between the center axial line, or axis, of the tooth as measured and displayed and the coded torque information for the bracket associated with that tooth in accordance with the particular orthodontic bracket selected by the orthodontist. If there is no difference between the displayed center axis of the tooth and the coded image of the tooth as determined at step 38, the program branches to and performs the same comparison for the next tooth which is initiated at step 40 until it is determined that all teeth have the proper torque value.

If at step 38 it is determined that there is a difference between the position and orientation of the tooth's center axis and the coded image of the tooth on the display representing the desired position of the tooth, the program proceeds to step 42 for tipping the tooth to its correct torque value on the video display so that the BSP on each tooth is located at a predetermined distance from the lingual surface of the archwire. The predetermined distance of each tooth's BSP from the arch wire is based on values taken from published values of prominence for commercially available bracket systems. For an individual patient, these values will be taken from the bracket system indicated for that patient's treatment. The three-dimensional rotations of the teeth described herein are performed with the BSP serving as the rotation base point. All tooth rotations are accomplished in concert with the patient's X-rays as a reference to root positioning/support considerations. In the teeth reorientation procedure described below, the anterior teeth are rotated so that their incisal edges are normal to the local curvature of the arch wire as the teeth are viewed from the incisal. The bicuspid teeth are rotated so that both cusps are equidistant from the archwire when viewed from the incisal. The molars are rotated according to the published "distal rotation specifications" of the brackets/buccal tubes selected for the individual patient's treatment when viewed from the incisal. The disto-buccal cusp will typically be further offset from the arch wire than the mesial cusp according to the predetermined "distal rotation" angle specifications for the alliance system. In measuring torque values, the distance between a vertical line passing through the BSP perpendicular to the plane described with respect to step 22 and a generally vertical line tangent to the cinical crown at the BSP point as seen from the mesial or distal view is determined. The number of degrees each tooth is tipped on the video display is dependent on the ideal torque value machined into the arch slot of each bracket.

Next, a comparison is made at step 44 between the center axis of the tooth with the coded angulation information for the particular set of orthodontic brackets selected. If at step 46 it is determined that there is no difference between the axial center line of the tooth and the coded angulation information for the selected orthodontic bracket stored in the computer's memory, the program branches to step 48 and initiates a comparison of the axial centerline of the next tooth with the coded angulation information for the bracket attached to that tooth. If at step 46 it is determined that there is a difference between the position and orientation of the axial centerline of the tooth and the coded angulation information for its associated bracket, the program branches to step 51 for rotating the tooth as shown in FIG. 11 to correct its angular value. Like torque, the angulation information for properly positioning and aligning the tooth is specified for the particular orthodontic bracket selected, with angulation values measured between a line perpendicular to the plane described in step 22 and the vertical axis of the clinical crown as seen from the labial-lingual view. This routine continues until all teeth have the proper angular value.

At step 53, the interproximal contact points of the teeth are examined and the modified positions of all of the teeth are now further adjusted in a "fine tuning" step in terms of intrusion/extrusion and labial/lingual translation to establish solid and stable interproximal contact points between the virtual teeth as presented on the video display. This procedure involves small "fine tuning" repositioning movements of the teeth to accommodate the unique variations of tooth morphology of the individual patient.

At step 55, the upper set of virtual teeth is repositioned over the lower set of virtual teeth and the upper and lower sets of teeth are brought into occlusion (into bite contact). The "fit" of the upper and lower arches is then analyzed gnathologyically to identify combinations of teeth that provide significant interference, or teeth which simultaneously occupy the same space. Such situations require the CAD/CAM technician to again subtly reposition some of the teeth in terms of intrusion/extrusion and labial/lingual translation to avoid significant interference and to provide for a more natural and stable interdigitation of the arches. This involves a second "fine tuning" repositioning movement of the teeth at step 57 to accommodate the unique variations of tooth morphology of the individual patient. This procedure is repeated with the teeth placed in right laterotrusion and again in left laterotrusion (right and left chewing positions). The upper and lower virtual models of the teeth are again repositioned so that the occlusal edges of the teeth are "up."

At step 59, a complete set of typically 20 orthodontic brackets and eight buccal tubes is then unblanked on the video display. The orthodontic brackets and buccal tubes are the components of the "prescription" chosen as most appropriate to treat an individual patient. Full engineering representations of the appliances were previously created and stored in the computer memory using the CAD/CAM software for use at this point in the inventive method. The virtual appliances are introduced into the three dimensional virtual space at precisely the same scale (size) as models of the patient's teeth. At step 61, each tooth-specific bracket and buccal tube is properly positioned so that it fully engages the arch wire at a point adjacent to its respective or molar. The center of the bracket base is positioned precisely over the previously determined BSP. For molars, a point on the base directly below the center of the mesial end of the arch slot as positioned above the molar BSP. The relationship of the bonding base of the appliance to the surface of the crown for all teeth is then analyzed. Because of variations in individual tooth anatomy and the small repositioning of the teeth as accomplished in previous described steps 53 and 57, the bonding bases of the appliances will likely not evenly contact the tooth crown. For some teeth, a gap between the enamel of the crown will likely be present whereas in other cases, the virtual base may "violate" (simultaneously occupy the same space with) the crown.

At step 63, those teeth having significant "violations" (or occupying the same space as its associated tooth) are repositioned by means of minor labial/lingual translations to eliminate gaps between and overlapping of upper and lower sets of the teeth. Teeth exhibiting gaps between the bonding base and the crown are acceptable with this method and do not require repositioning. The entire screen consisting of the display of the virtual model of the patient's teeth, the two arch wires, and the 28 orthodontic appliances as positioned in contact with their respective teeth is then saved in the computer memory in a designated patient specific file. If the upper teeth occlude on the brackets of the lower teeth, steps 55 to 63 may be repeated, with the lower brackets in a more gingival position, if possible. If not, the clinician is notified and the clinician needs to determine whether to go ahead and place all the brackets initially or in various stages of treatment. The virtual model of the properly positioned teeth as presented on the video display is thus saved and stored in memory for subsequent recall and use. At step 65, the video display is unblanked for one virtual tooth as well as its associated bracket. The orthodontic bracket and tooth will be precisely positioned relative to each other as previously described. At step 67, a "quilt" is installed over the entire surface of the displayed tooth. A quilt is a CAD/CAM term referring to a modification of a previously created surface that allows that surface to be used in subsequent operations where only part of that surface will be used. The generation and use of quilts is well known in computer graphics and is a commonly used tool in CAD/CAM applications. The quilt represents the original digitized (scanned) natural undulating surface of the patient's tooth. The jig preform is then unblanked at step 69 and the virtual jig is installed on the virtual bracket so that the bracket engaging features of the jig positively and fully align with and engage the orthodontic bracket. The virtual jig preform is configured so that in all cases, when positioned on its associated orthodontic bracket, it will "violate" (and simultaneously occupy the same space of) the crown of even the statistically most underdeveloped tooth. The portions of the quilt that fall outside of the external peripheral borders of the jig are removed, or cut, from the quilt. All lines defining the edges of the jig that violate the quilt are removed. These last two steps in essence involve attaching the tooth to the tooth-engaging area of the positioning jig at step 71. The remaining portion of the quilt is attached to the trimmed edges of an orthodontic jig and all material that violates the tooth is removed from the jig. Steps 65–71 are repeated for all 28 teeth and the thus generated custom jigs are stored in memory at step 73. At step 75, the first jig is unblanked and using the quilt for its associated tooth, a negative of the tooth surface adjacent the engaging area of the jig is presented on the video display.

Figure 13:
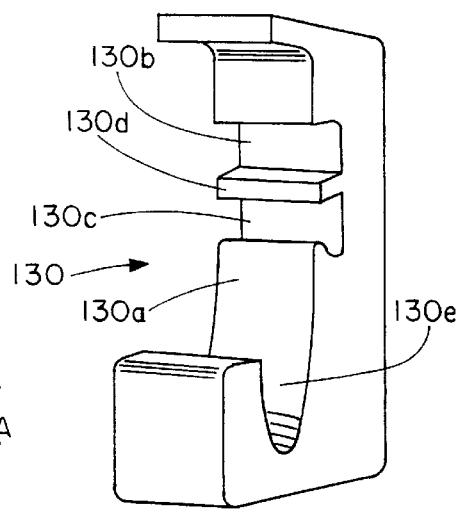
FIG. 13 is a perspective view of a positioning jig custom configured by means of the present invention for attaching an orthodontic bracket to a tooth.
Figure 14:
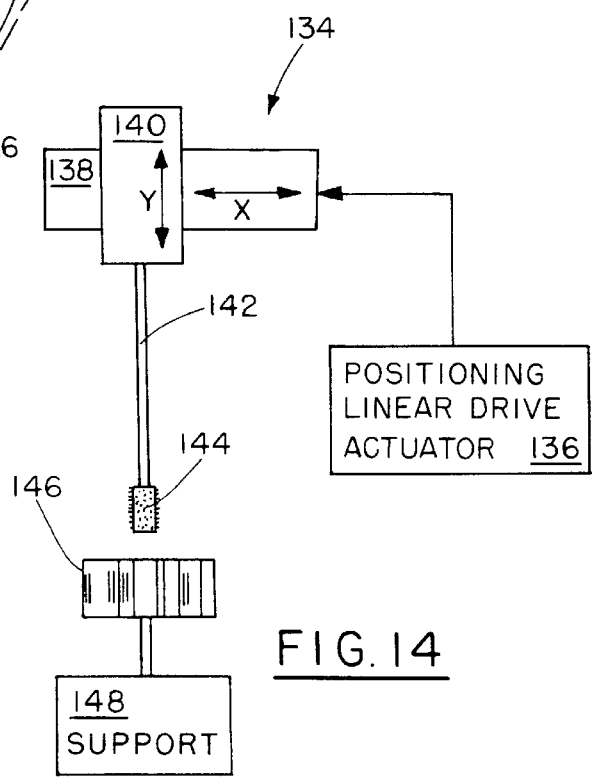
FIG. 14 is a simplified combined schematic and block diagram of a computer numeric control (CNC) apparatus for forming an orthodontic jig in accordance with the principles of the present invention.

The next step 77 involves providing the data representing the optimum size and shape of each orthodontic bracket positioning jig to a computer controlled numerical (CNC) milling machine 134 such as shown in FIG. 14 for forming 20 to 24 jigs, such as the orthodontic bracketing position jig 130 shown in the perspective view of FIG. 13. Using the CAM portion of the software to install an appropriate set of tool paths over the portion of the virtual jig that is defined by the aforementioned quilt, a negative of the unique tooth surface features in the tooth engaging area of the jig is reproduced. Tool paths are installed in the tooth engaging area for the remaining 27 virtual jigs. These tool paths are then stored in memory and become the "file" of the individual patient. Using the CNC data from the patient's file, the CNC milling machine 134 forms 28 custom jigs. During machining, the jigs are individually coded to identify to which one of the patient's teeth it is to be attached.

Positioning jig 130 shown in FIG. 13 is representative of a typical orthodontic positioning jig. Jig 130 is preferably comprised of a somewhat flexible, resilient material to permit the jig to securely receive and engage an orthodontic bracket (not shown in the figure) in a snap-acting manner for insertion on a tooth in a tight-fitting manner. The flexible, resilient jig 130 can then be removed from the bracket and tooth with the application of a predetermined amount of force leaving the bracket bonded to the tooth. Jig 130 includes an inner contoured surface 130*a* and a lower recessed portion 130*e*. The inner contoured surface 130*a* engages a lateral portion of the tooth while the lower contoured surface 130*e* engages the distal end portion of the tooth. The orthodontic jig 130 further includes upper and lower recesses 130*b* and 130*c* and a finger portion 130*e* disposed between the two recesses. An upper and lower recess 130b, 130c accommodate spaced projections on the orthodontic bracket, while the jig finger portion 130e forms a slot between the upper and lower projections of the bracket. The jig finger portion 130d adapts to the bracket archwire slot. It is via the archwire slot that the tooth is positioned by the forces from the archwire.

Referring to FIG. 14, there is shown a simplified combined block and schematic diagram of a jig forming machine 134 for forming a custom orthodontic jig in accordance with the present invention. The jig forming machine 134 includes a support mechanism 148 attached to an orthodontic jig blank 146 for supporting and maintaining the jig in fixed position. The jig forming machine 134 further includes a cutting blade 144 disposed on the distal end of a rotating shaft 142. The shaft 142 is coupled to and displaced by X-axis and Y-axis position transducers 138 and 140 as well as by a Z-axis positioning transducer which is not shown in the figure for simplicity. The X-axis and Y-axis position transducers 138, 140 are coupled to and displaced by a positioning linear drive actuator 136. Linear drive actuator 136 is coupled to and driven by the computer in which is stored the size and dimension data of the jig for optimum positioning of the jig and its associated orthodontic bracket on a given tooth as determined at step 60 described above. Cutting blade 144 is used to form an orthodontic jig such as shown in FIG. 13 from the orthodontic jig blank 146 shown in FIG. 14. Steps 75 and 77 are repeated at step 77 for all 28 teeth producing 28 virtual custom jigs.

Figure 15:
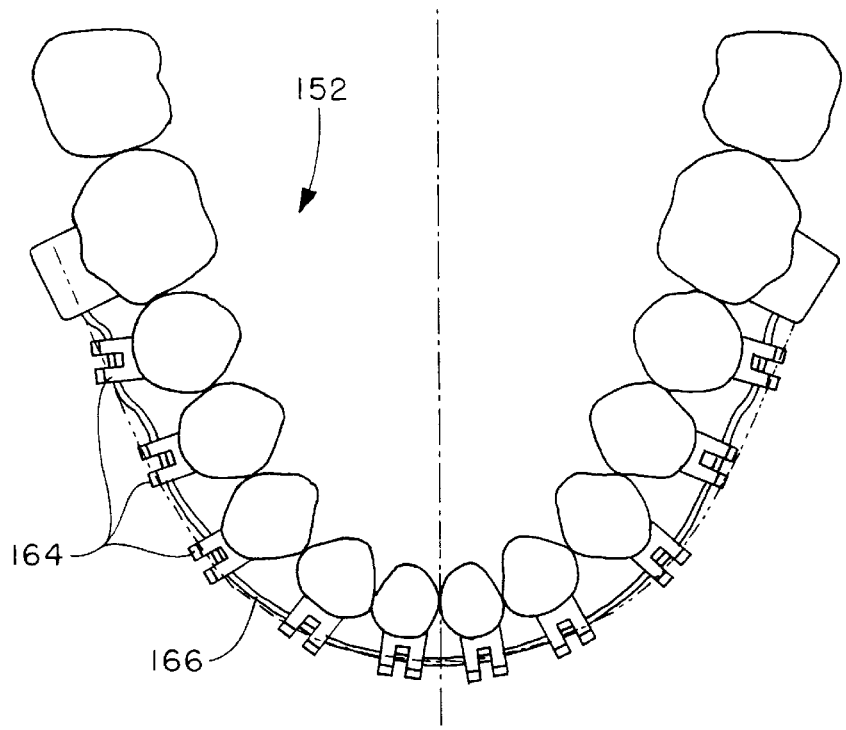
FIG. 15 is a plan view of a set of teeth showing an orthodontic bracket attached to each tooth and an archwire attached to each bracket for straightening and/or realigning the teeth.

Each jig is attached to its associated orthodontic bracket and a complete set of jig/bracket combinations is packaged in a multi-cavity shipping tray and forwarded to an orthodontist at step 81. Next, an adhesive is applied to each bracket at step 83 by the orthodontist or may be applied when the jig/bracket combinations are packaged earlier at step 81 in attaching each bracket and buccal tube to its associated jig. Each jig is then installed on its associated tooth at step 87 using the orthodontic bracket to which the jig is coupled in bonding the brackets and buccal tubes to the teeth. The jig/bracket combination is securely maintained in position on the tooth by means of the aforementioned adhesive applied to the bracket. Each jig "locks" onto its associated tooth as it has been accurately machined to fit that tooth. Each bracket is positioned on its associated tooth exactly as previously viewed on the video display even though at the beginning of treatment the tooth may be far from its desired finished location and orientation. A light beam is then directed onto the adhesive deposit for curing the adhesive and fixedly attaching the bracket to its associated tooth. The jig is then removed from the tooth and orthodontic bracket combination at step 89. Upper and lower archwires are then attached to respective upper and lower sets of orthodontic brackets at step 93, with each archwire applying a predetermined force on each maloccluded tooth as shown for the set of teeth 152, a set of orthodontic brackets 164 and an archwire 166 in the plan view of FIG. 15.

Figure 16:
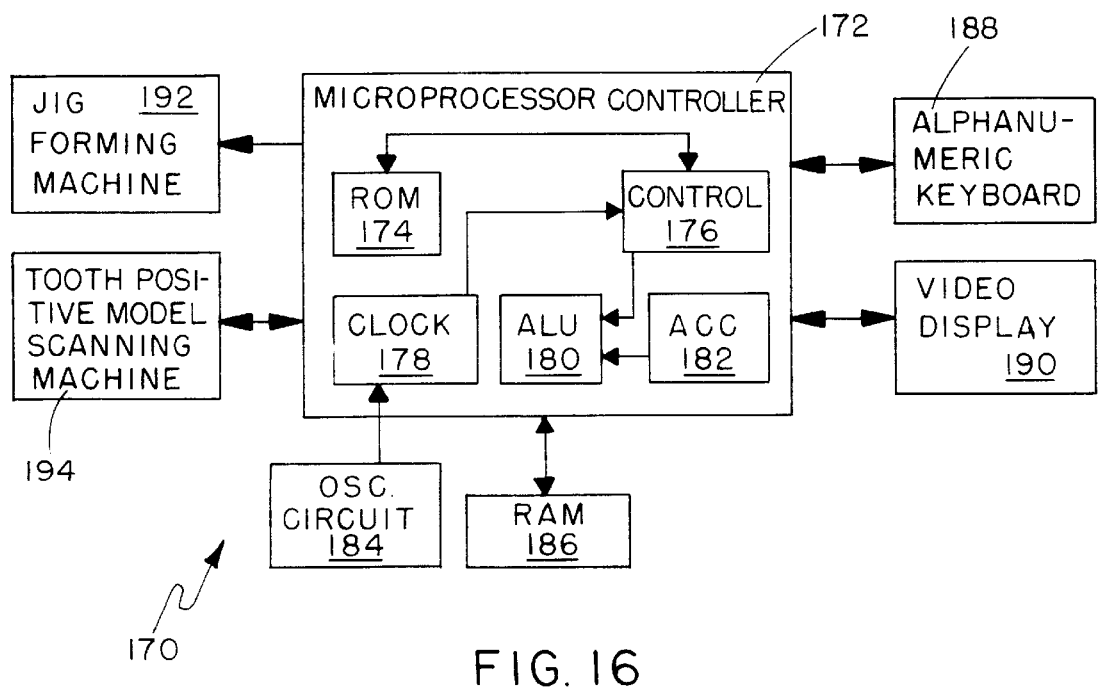
FIG. 16 is a simplified block diagram of an orthodontic jig measuring and fabrication system for the design and fabrication of custom orthodontic jigs used in the attachment of orthodontic brackets to a plurality of a patient's teeth in accordance with the principles of the present invention.

Referring to FIG. 16, there is shown a block diagram of an orthodontic jig measuring and fabrication system 170 in accordance with the present invention. The jig measuring and fabrication system 170 includes a microprocessor controller 172 coupled to various peripherals for receiving control inputs from these peripherals and providing control outputs to the peripherals in carrying out the jig measuring and fabrication functions described in detail above. The microprocessor controller 172 may be conventional in design and includes a read only memory (ROM) 174, a controller 176, a clock 178, an arithmetic and logic unit (ALU) 180, and an accumulator (ACC) 182. Microprocessor controller stores instructions and data, periodically updates the stored data, compares both stored and realtime data and makes decisions based upon these comparisons by means of logic instructions in providing for control of the jig measuring and fabrication system 170. ROM 174 is a nonvolatile, factory produced memory matrix for storing data and instructions.

An oscillator circuit 184 external to the integrated circuit (IC) microprocessor controller 172 provides timing signals to clock 178 for controlling the timing of the operations carried out by the microprocessor. When power is applied to the microprocessor controller 172, the microprocessor program stored in ROM 174 causes binary signals representing a first instruction stored in the ROM to be provided to the controller 176 for proper initialization of the microprocessor controller. ALU 180 receives binary control signals from controller 176 and performs the required arithmetic or logic operation. User entries are made to the microprocessor controller 172 by means of a user operated alphanumeric keyboard 188. Keyboard 188 is continuously scanned by the microprocessor controller 172 for the detection of entries thereon. A video display 190 is coupled to the microprocessor controller 172 for receiving and processing digital display signals in presenting a video image of the patient's teeth in their present position and orientation as well as in the desired position and orientation. Data entered via keyboard 188 and provided to microprocessor controller 172 is stored in a random access memory (RAM) 186. Microprocessor controller 172 thus writes data into RAM 186 for storage therein and reads, or recalls, stored data from the RAM in controlling the operation of the orthodontic jig measuring and fabrication system 170. Microprocessor controller 172 is also coupled to and receives inputs from a tooth positive model scanning machine 194 such as shown in FIGS. 6 and 7 and described above. Microprocessor controller 172 also provides control signals to the tooth positive model scanning machine 194. Finally, microprocessor controller 172 provides control signals for controlling the operation of a jig forming machine 192 such as shown in FIG. 14 and described in detail above.

There has thus been shown an orthodontic bracket system and method therefor including an orthodontic jig measuring and fabrication apparatus. The present invention allows the orthodontist not only to allow inclusion of variable tooth anatomy into idealized bracket placement, but also to include for the first time the other factors which determine a non-traumatic, properly functioning occlusion for a specific individual. Samples of some average measurements achieved by the present invention are shown in Table I. These measurements represent a substantial improvement over prior art approaches. In Table I, the angles listed are the angles formed with the axis-orbital plane, which is a plane formed by a line from the center of rotation of the mandibular condyle and the lower margin of the orbit of the eye (referred to as orbital). This plane is equivalent to the superior surface of an articulator. Subtracting 7° from the axis-orbital plane yields an approximate Frankfort-Horizontal plane, a well known orthodontic reference plane, measurable from a cephalogram. For example, as above, in a Class I skeletal relation, the occlusal plane is 13° to the axis-orbital plane and 6° to the Frankfort plane.

TABLE I

| Skeletal Relation | Molar Cusp Angle | Occlusal Plane Angle | Horizontal Condyle Inclination | Incisal Guidance |
|---|---|---|---|---|
| Class I | 23° | 13° | 52° | 62° |
| Class II | 23° | 16° | 55° | 64° |
| Class III | 23° | 8° | 47° | 56° |

In Class I, the upper and lower jaws are harmonious.
In Class II, the upper jaw is in front of the lower jaw.
In Class III, the lower jaw is in front of the upper jaw.

In the present invention, a negative impression of a patient's teeth is made, from which a positive hard duplicate pattern, sometimes referred to as a "stone model," of the teeth is formed. A bite registration reflecting the movement pattern of the mandible is taken. A digitized three dimensional coded image of the teeth is then generated by means of a coordinate measuring machine or by laser scanning for measuring and displaying a central axis of each tooth on a video display. An exploded image of the set of teeth is then presented on the video display, with each tooth moved in virtual space to a desired position and orientation using torque, tip and angulation values as well as in/out position information provided by the selected orthodontic bracket system. The optimum position for each tooth-mounted orthodontic appliance bracket and its attachment point to its associated tooth is determined for moving each tooth to a desired orientation and position. A digitized coded image of the tooth including its central axis is compared with the aforementioned torque, tip and angulation values in comparing its initial and final desired position and orientation. Using the orthodontic bracket attachment information for each tooth, the shape and contour of a bracket attachment jig is determined for each tooth and its associated orthodontic bracket. This digital information is used to fabricate a plurality of such jigs under computer control such as by means of a computer numeric control (CNC) milling machine. A custom shaped jig is then used for attaching its associated conventional orthodontic bracket to a tooth at an optimum location for moving the tooth to a desired position and orientation. Once the orthodontic bracket is attached to a designated tooth, the jig is removed from the tooth and bracket combination. The orthodontic brackets are conventional in size and shape as are a pair of archwires attached to the upper and lower optimally positioned brackets. The archwires urge each tooth to its respective desired position and orientation with minimal subsequent manipulation and adjustment of the archwires by the orthodontist.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation.

The actual scope of the invention is intended to be defined in the following claims when viewed in their proper perspective based on the prior art.

I claim:

1. A method for installing conventional orthodontic brackets and an archwire on a set of teeth, said method comprising the steps of:

forming a positive hard duplicate pattern of a patient's set of teeth;

scanning said positive hard duplicate pattern for providing a digitized three dimensional coded video image of the set of teeth and storing said digitized coded video image in a memory;

displaying a center axis of each tooth in the set of teeth, wherein said center axis extends between a root portion and a crown portion of the tooth;

determining differences between the position and orientation of the center axis of each tooth and torque, tip and angulation values for each tooth representing a desired position and orientation of the tooth for a selected set of orthodontic brackets;

determining differences between the digitized three dimensional video image and a statistically average tooth for each tooth;

determining an optimum position of each bracket on an associated tooth for moving the tooth to said desired position and orientation;

determining a size and shape of a positioning jig for each bracket and tooth combination for optimum positioning of each bracket on a respective tooth for moving the tooth to said desired position and orientation;

attaching each jig to an associated bracket and installing each jig and bracket combination on a respective tooth in said optimum position;

removing each jig from its associated bracket; and attaching an archwire to said brackets.

2. The method of claim 1 wherein the step of scanning said positive hard duplicate pattern of the patient's set of teeth includes tracing over the teeth with a coordinate measuring machine having a probe tip engaging and moving across the surface of each of the teeth.

3. The method of claim 1 wherein the step of scanning the positive hard duplicate pattern of the patient's set of teeth includes directing a laser beam onto said teeth and moving the laser beam over the surface of each tooth.

4. The method of claim 1 wherein the step of displaying a center axis of each tooth includes displaying an exploded view of the set of teeth showing the center axis of each tooth.

5. The method of claim 1 wherein the step of determining differences between the position and orientation of the center axis of each tooth and torque, tip and angulation values for each tooth includes loading digitized coded torque and angulation information for various sets of conventionally sized and shaped orthodontic brackets into a digital computer.

* * * * *